United States Patent
Teed

[11] 3,951,151
[45] Apr. 20, 1976

[54] DISPOSABLE DIAPER
[75] Inventor: Richard K. Teed, Greenwood, S.C.
[73] Assignee: Riegel Textile Corporation, New York, N.Y.
[22] Filed: Apr. 15, 1974
[21] Appl. No.: 460,916

[52] U.S. Cl. ............................................. 128/287
[51] Int. Cl.[2] ....................................... A61F 13/16
[58] Field of Search .......... 128/284, 286, 287, 290, 128/296

[56] References Cited
UNITED STATES PATENTS

| | | | |
|---|---|---|---|
| 3,065,751 | 11/1962 | Gobbo, Sr. et al. ................ | 128/287 |
| 3,211,147 | 10/1965 | Pherson et al. ..................... | 128/284 |
| 3,295,526 | 1/1967 | Sabee................................ | 128/287 |
| 3,636,952 | 1/1972 | George .............................. | 128/287 |
| 3,777,759 | 12/1973 | Oehmke et al. ..................... | 128/287 |

*Primary Examiner*—John D. Yasko
*Assistant Examiner*—Rick Opitz
*Attorney, Agent, or Firm*—Bell, Seltzer, Park & Gibson

[57] ABSTRACT

The improvements, in a disposable diaper including a fluid permeable top sheet and a fluid impermeable bottom sheet bound and secured together along their transverse and longitudinal edges and having a fluid absorbent pad disposed between the top and bottom sheets and including several layers of cellulose wadding and a layer of fiberized pulp disposed between the cellulose wadding layers, as follows. The top and bottom sheets are bound together along their transverse edges by means of short, spaced, glue lines extending transversely to and spaced along the transverse edges of the disposable diaper for providing soft, flexible, transverse edges to the diaper for comfort when placed in position on the wearer. Longitudinally-extending, thin, narrow, embossed lines in the wadding layers hold the several layers together and effectively enclose the fiberized pulp layer between the cellulosic wadding layers to prevent dislocation of the fiberized pulp layer during use of the diaper.

3 Claims, 2 Drawing Figures

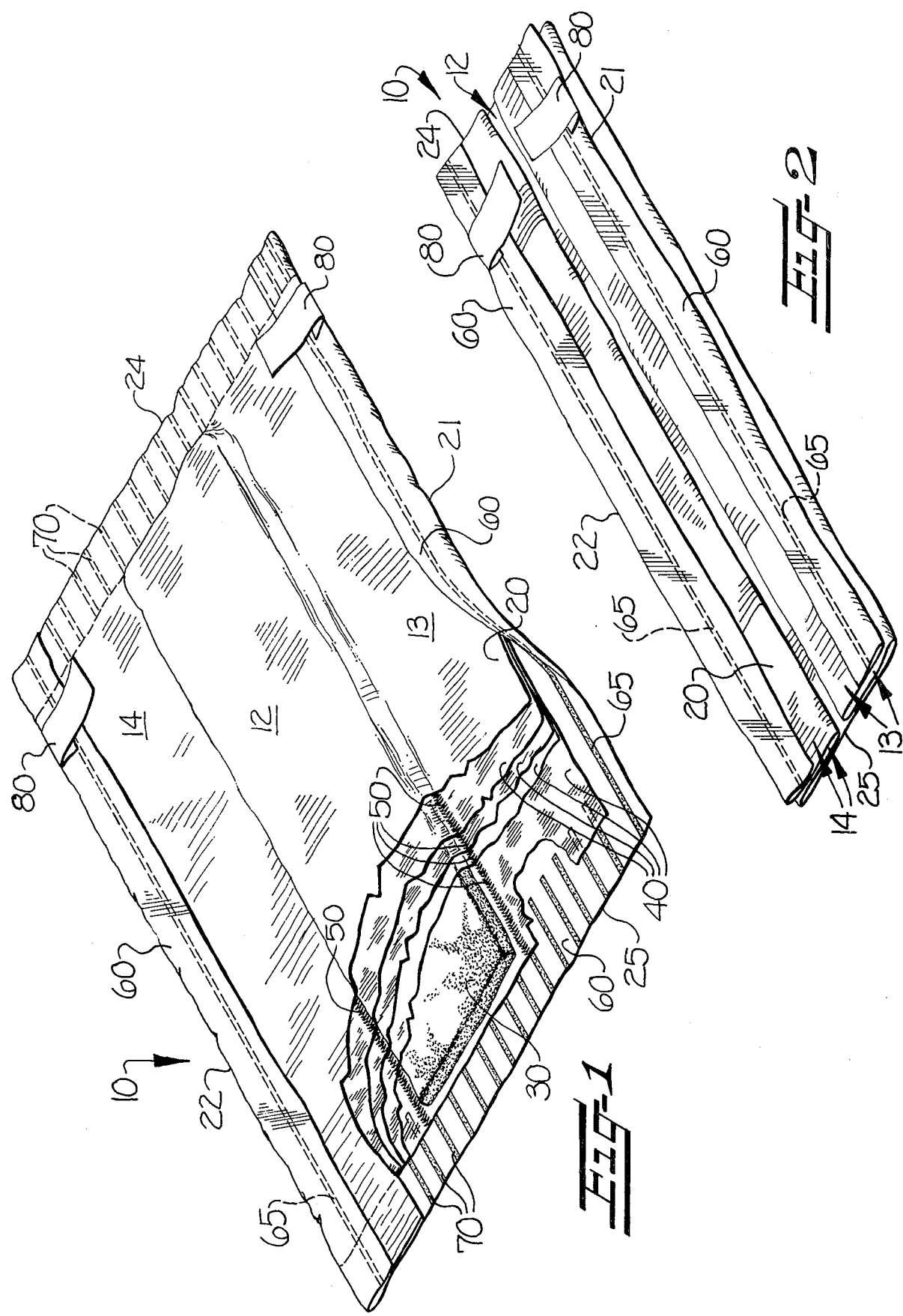

DISPOSABLE DIAPER

BACKGROUND AND SUMMARY OF THE INVENTION

In U.S. Pat. No. 3,636,952, issued Jan. 25, 1972, which is owned by the same assignee as the present invention, there is disclosed a disposable diaper consisting essentially of paper and comprising a special water permeable cellulosic top layer for contact with the baby's skin, a waterproof thin plastic bottom layer and an intermediate moisture absorbent pad containing several layers of paper wadding and a layer of fiberized pulp having high moisture absorbent properties.

The above-mentioned top layer, which is made of a special form of cellulosic fibers, and the fiberized pulp layer, which has a superior high loft, softness and freedom from knots and dust, have contributed substantially to the commercial success of the disposable diaper. This special top layer component is covered by U.S. Pat. No. 3,171,773, issued Mar. 2, 1965. And the superior fiberized pulp component is covered by U.S. Pat. Nos. RE26,939, issued Aug. 18, 1970, 3,554,862, issued Jan. 12, 1971 and 3,554,863, issued Jan. 12, 1971. All of these patents are assigned to the same assignee as the present application and identify an extensive line of research and development in the disposable diaper field.

The commercial diaper product disclosed in said U.S. Pat. No. 3,636,952, issued Jan. 25, 1972, has been the subject of further research and has been markedly improved in accordance with the present invention. Two important features are (a) combining of the top and bottom sheets along the transverse edges of the disposable diaper in a secure yet soft and comfortable manner, and (b) an arrangement for maintaining the fiberized pulp layer in a permanent stable position in the disposable diaper. The prior problems and their solution by the present invention are identified somewhat more in detail as follows:

COMBINING OF TOP AND BOTTOM LAYERS ALONG THE TRANSVERSE EDGES

In the form of the disposable diaper disclosed in the above U.S. Pat. No. 3,636,952, the transverse edges of the diaper contained the top and bottom layers and the intermediate cellulose wadding layers and were secured together by means of pressing, i.e. embossing. This provided a stable leak-proof form of edge binding but had the objections of being relatively hard and stiff with resultant discomfort to the baby. These objections have been fully overcome in accordance with the present invention by an equally stable yet thin, soft flexible edge binding. In this new arrangement, substantially only the top and bottom sheets are included in the bound edge, the intermediate paper plies or cellulose wadding layers terminating somewhat short of the transverse edges. The top and bottom sheets are combined and securely held together by means of spaced, thin short glue-lines which extend transversely to the transverse edges and hold the top and bottom sheets firmly together without any stiffening or hardening.

STABILIZING OF THE FIBERIZED PULP SHEET IN THE DIAPER

In the form of diaper shown in the above U.S. Pat. No. 3,636,952, the fiberized pulp layer was held loosely between superimposed and underlying cellulose wadding sheets and was free to move between these sheets. In some uses of the disposable diaper product having this arrangement, the fiberized pulp layer tended to move from its original position and was subject to lumping especially when it became wet. This problem has been solved in accordance with the present invention by embossing along narrow lines of the cellulose wadding layers disposed above and below the fiberized pulp layer with the result that all of these layers remain substantially in tact and not subject to dislocation during use of the diaper.

BRIEF DESCRIPTION OF THE DRAWINGS

Some of the objects and advantages of this invention having been stated, other objects and advantages will appear, when taken in conjunction with the accompanying drawings, in which:

FIG. 1 is a perspective view of the improved disposable diaper construction in accordance with the present invention and illustrating components thereof broken away for clarity; and FIG. 2 is a perspective view of the improved disposable diaper construction of FIG. 1 shown in the prefolded condition thereof.

DESCRIPTION OF PREFERRED EMBODIMENT

Referring now to the drawings, the disposable diaper of this invention is generally referred to by the reference numeral 10 and is illustrated in FIG. 1 in its unfolded condition and in FIG. 2 in its preferred prefolded condition for easy application and fit onto the wearer. The features of this diaper 10 which are common to the aforementioned United States Patents of the assignee of the present invention will be described only broadly herein and reference may be had to these prior patents.

In its unfolded condition, the disposable diaper 10 has a generally rectangular configuration and defines longitudinally extending central portion 12 and side portions 13 and 14. For prefolding the disposable diaper 10, the side portions 13 and 14 (as shown in FIG. 2) are folded inwardly over the central portion 12 and then folded outwardly back over themselves.

Referring now particularly to FIG. 1, the disposable diaper 10 comprises a fluid-permeable, top, cover layer 20 of sheet material for being placed in contact with the body of the wearer and for receiving and passing therethrough the moisture of the wearer. The top cover layer 20 has generally the same dimensions, length and width, of the unfolded diaper 10.

The disposable diaper 10 further comprises a moisture-absorbing, interior pad positioned under the top cover layer 20 for absorbing the moisture of the wearer received through the top cover layer 20.

The interior pad comprises generally a layer or batt of fiberized fibers 30 having a width less than the width of the unfolded diaper 10 and is disposed in the central portion 12 of the diaper 10 only for concentrating absorbency therein and for providing relatively unbulky side portions 13 and 14 to allow easy folding of the diaper in the manner described above. As may be seen in FIG. 1, the width of the layer of fiberized fibers 30 is approximately one-third the width of the unfolded diaper 10 so that the layer 30 will be positioned in the central portion 12 of the unfolded diaper 10 only. The layer of fiberized fibers 30 has a longitudinal length slightly less than the longitudinal length of the diaper 10 so that the transverse edges of the fiber layer 30 terminates short of the transverse edges 24, 25 of the diaper 10 for reducing the bulk of the diaper 10 at these transverse edges to aid in securing the various components of the diaper 10 together. The absence of the fiber layer 30 in both the transverse edges 24, 25 and the longitudinal edges 21, 22 of the diaper 10 provide unbulky edges around the entire diaper 10 for aiding in a better fit of the diaper 10 onto the wearer.

The interior pad further comprises interior sheets or layers 40 of cellulose wadding material including one sheet 40 positioned below the layer of fiberized fibers 30 and a plurality of sheets 40 positioned on top of the fiber layer 30 and under the top cover sheet 20 for forming an interior envelope around the fiber 30 to provide strength to and stabilize the fiber layer 30 and provide additional absorbency to the diaper 10. The interior sheets 40 have a width substantially the same as the unfolded diaper 10 for providing absorbency throughout the width of the diaper 10 and in the side portions 13, 14 thereof which preferably do not include the fiber layer 30. The interior sheets 40 have a length less than the length of the diaper 10 so that the transverse outer edges of the interior sheets 40 terminate short of the transverse edges 24, 25 of the unfolded diaper 10 to aid in securing the various components of the diaper together. In the form of the diaper 10 illustrated in the drawings, there is shown three interior sheets 40 positioned on top of the fiber layer 30; however, it is to be understood that an additional number or a less number of sheets may be utilized here.

In accordance with the present invention, the improved construction of the disposable diaper 10 includes longitudinally extending embossed lines or areas 50 securing all of the interior sheets 40 together on each side of the longitudinal edges of the layer of fiberized fibers 30 for providing a tight enclosure for the fiber layer 30 to retain the fiber layer 30 in position in the central portion 12 of the unfolded diaper 10 and to prevent transverse shifting of the fiber layer 30 within the diaper 10 during wear and use of the diaper. These embossed areas 50 may be formed by any well known embossing mechanism and this procedure is well known by those with ordinary skill in the art and need not be further explained herein for an understanding of the present invention.

The disposable diaper 10 further includes a protective, fluid-impermeable, bottom, cover layer 60 of sheet material positioned under the interior pad to form with the top cover layer 20 an envelope around the interior pad. The bottom cover layer 60 would be positioned away from the skin of the wearer when the diaper 10 is positioned on the wearer and would therefore retain the moisture of the wearer within the diaper 10.

A longitudinally-extending line of glue 65 is positioned along each longitudinal edge 21, 22 of the diaper 10 between the top cover layer 20 and an overlapping portion of the bottom cover layer 60 for securing these layers together along the longitudinal edges 21, 22 of the diaper 10.

A plurality of short, spaced-apart, generally longitudinally-extending, glue lines 70 extend from each outer transverse edge 24, 25 of the unfolded diaper 10 inwardly between the top cover layer 20 and the bottom cover layer 60 and terminate slightly inside the outer transverse edges of the interior sheets 40 for securing the top cover layer 20 and the bottom cover layer 60 together and for securing the interior sheets 40 thereto along the transverse edges 24, 25 of the unfolded diaper. These spaced-apart glue lines 70 provide soft, flexible, transverse edges 24, 25 to the diaper 10 for comfort when placed in position on the wearer, yet provide securement between the top cover layer 20, the bottom cover layer 60 and the interior sheets 40.

If desired, the disposable diaper 10 may include a pair of elongate securing tabs 80 on each longitudinal edge 21, 22 of the diaper 10.

In the drawings and specification there has been set forth a preferred embodiment of the invention and, although specific terms are employed, they are used in a generic and descriptive sense only and not for purposes of limitation.

What is claimed is:

1. In a disposable diaper having longitudinal and transverse edges comprising a fluid permeable top sheet, a fluid impermeable bottom sheet, a fluid absorbent pad of less length than said top and bottom sheets and being disposed between said top and bottom sheets and terminating in outside ends short of said transverse edges of said diaper, and means for securing said top and bottom sheet along said longitudinal edges; the improvement of:

a plurality of short, spaced-apart, generally longitudinally-extending glue lines extending from each of said outer transverse edges of said diaper inwardly between said top cover sheet and said bottom cover sheet and at least slightly inwardly of said outside ends of said absorbent pad and being spaced along substantially the entire length of said transverse edges of said diaper for securing said top cover layer and said bottom cover layer together at said glue lines only and for securing said interior pad thereto along the transverse edges of said diaper for providing soft, flexible, transverse edges to said diaper for comfort when placed in position on the wearer.

2. In a disposable diaper comprising a fluid permeable top sheet and a fluid impermeable bottom sheet bound together along their transverse and longitudinal edges, and a fluid absorbent pad disposed between said top and bottom sheets and comprising several layers of cellulose wadding and a layer of fiberized pulp disposed between said cellulose wadding layers and being of less width than said wadding layers; the improvement of:

longitudinally-extending, thin, narrow, embossed lines in said wadding layers only and on each side of said fiberized pulp layer which hold the several layers together and effectively enclose said fiberized pulp layer between said cellulose wadding layers for preventing dislocation of said fiberized pulp layer during use of said diaper.

3. A disposable diaper of generally rectangular configuration having longitudinal and transverse edges comprising:

a fluid-permeable, top, cover layer of sheet material for being placed in contact with the body of the wearer and for receiving the moisture of the wearer and having generally the dimensions of said diaper;

a moisture-absorbing, interior pad positioned under said top cover layer for absorbing the moisture of the wearer received therethrough, said interior pad comprising a layer of fiberized pulp having dimensions less than the dimensions of said diaper so that the transverse and longitudinal edges of said fiber layer terminate short of the transverse and longitudinal edges of said diaper for reducing the bulk of said diaper at the edges thereof and interior sheets of cellulose wadding material positioned on each side of said fiber layer for forming an interior envelope around said fiber layer;

longitudinally-extending embossed areas in said interior sheets only for securing said interior sheets together on each side of the longitudinal edges of said fiber layer for retaining said fiber layer in position within said diaper and to prevent dislocation of said fiber layer within said diaper;

a protective, fluid-impermeable, bottom, cover layer of sheet material positioned under said interior pad to form with said top cover layer an envelope around said interior pad and for preventing moisture absorbed therein from passing out of said diaper and having a length the same as said diaper and having a width at least as wide as said diaper;

means securing said top cover layer and said bottom cover layer to each other along the longitudinal edges of said diaper; and a plurality of short, spaced-apart, generally longitudinally-extending glue lines extending from each outer transverse edge of said diaper inwardly between said top cover layer and said bottom cover layer and terminating slightly inside said interior sheets and being spaced along substantially the entire length of the transverse edges of said diaper for securing said top cover layer and said bottom cover layer together at said glue lines only and for securing said interior sheet thereto along the transverse edges of said diaper and for providing soft, flexible, transverse edges to said diaper for comfort when placed in position on the wearer.

* * * * *